United States Patent [19]

Sessions

[11] Patent Number: 5,722,943

[45] Date of Patent: *Mar. 3, 1998

[54] NON-STRETCHING WOUND DRESSING

[75] Inventor: Robert W. Sessions, Burr Ridge, Ill.

[73] Assignee: Ferris Mfg. Corporation, Burr Ridge, Ill.

[*] Notice: The portion of the term of this patent subsequent to Dec. 5, 2006, has been disclaimed.

[21] Appl. No.: 733,962

[22] Filed: Jul. 22, 1991

Related U.S. Application Data

[63] Continuation of Ser. No. 417,289, Oct. 5, 1989, abandoned, which is a continuation of Ser. No. 797,777, Nov. 12, 1985, Pat. No. 4,884,563, which is a continuation-in-part of Ser. No. 707,233, Mar. 1, 1985, abandoned.

[51] Int. Cl.$^6$ .............................. A61F 13/00; A61F 15/00
[52] U.S. Cl. ......................... 602/57; 206/440; 206/441; 128/851
[58] Field of Search ........................ 428/216, 424.6, 428/428.8; 206/440, 441; 604/304, 307, 308; 128/851; 602/57, 58; 606/214, 215, 216

[56] References Cited

U.S. PATENT DOCUMENTS

| | | | |
|---|---|---|---|
| 3,062,210 | 11/1962 | Scholl | 128/156 |
| 3,870,593 | 3/1975 | Elton et al. | 128/156 |
| 3,885,559 | 5/1975 | Economou | 128/156 |
| 4,265,234 | 5/1981 | Schaar | 602/57 |
| 4,334,530 | 6/1982 | Hassell | 128/156 |
| 4,374,520 | 2/1983 | Grossmann et al. | 128/851 |
| 4,600,001 | 7/1986 | Gilman | 604/307 |
| 4,619,253 | 10/1986 | Anhauser et al. | 128/156 |
| 4,706,662 | 11/1987 | Thompson | 128/156 |
| 4,875,473 | 10/1989 | Alvarez | 128/156 |
| 4,884,563 | 12/1989 | Sessions | 128/155 |

FOREIGN PATENT DOCUMENTS

| | | | |
|---|---|---|---|
| 2131299 | 6/1984 | United Kingdom | 602/57 |
| 2157955 | 11/1985 | United Kingdom | 602/57 |

*Primary Examiner*—Paul B. Prebilic
*Attorney, Agent, or Firm*—Leydig, Voit & Mayer, Ltd.

[57] ABSTRACT

A non-stretchable wound dressing has a flexible, non-stretching cover sheet having adhesive on one side thereof, and having two spaced strip-form gripping tabs at opposite ends thereof. The cover sheet covers a urethane wound dressing with the adhesive of the cover sheet being in contact with the urethane, and the urethane having an adhesive layer on an opposite side thereof. For storage and prior to application to a patient, the adhesive of the urethane wound dressing is in contact with a releasable surface of a carrier, such as cardboard. For application to a patient, one of the cover sheet gripping tabs is pulled so as to release the cover sheet and wound dressing from the carrier, the cover sheet preventing stretching of the wound dressing. The combination is then applied to a patient, with the adhesive of the wound dressing in contact therewith, again the cover sheet preventing stretching of the wound dressing. The other gripping tab of the cover sheet is then pulled to separate the cover sheet from the wound dressing, leaving the wound dressing on the patient with no stretching thereof. An optional third gripping tab and minor cover sheet may be located beneath the second gripping tab.

26 Claims, 4 Drawing Sheets

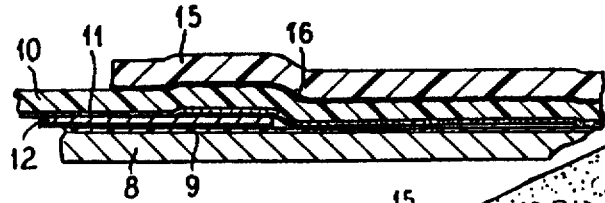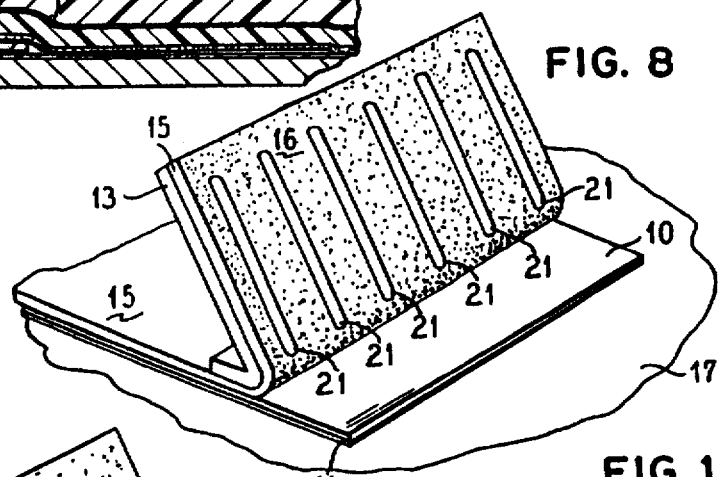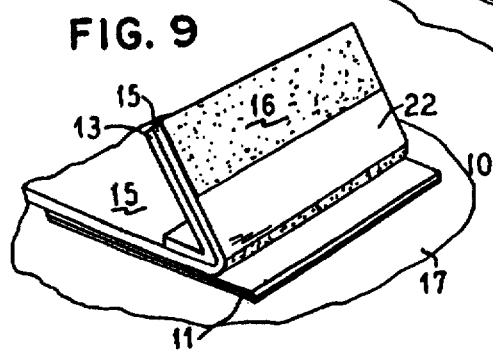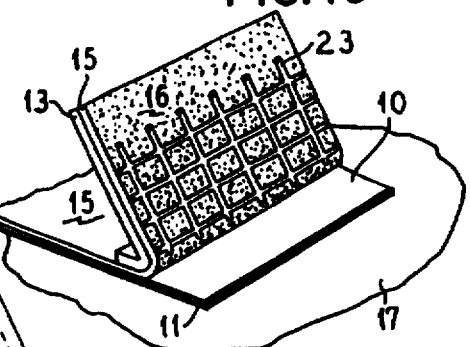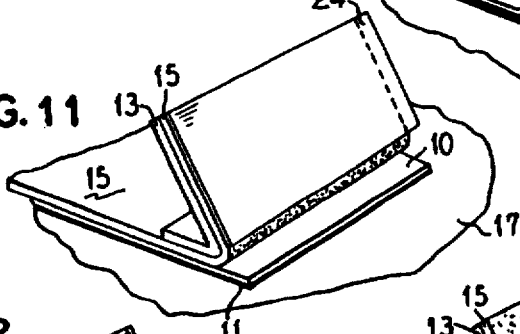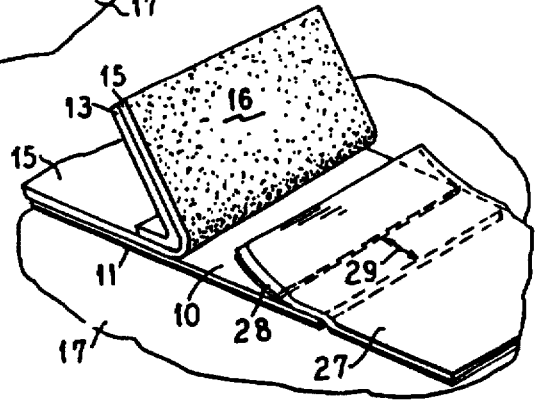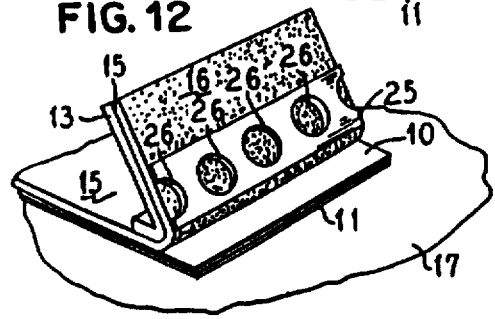

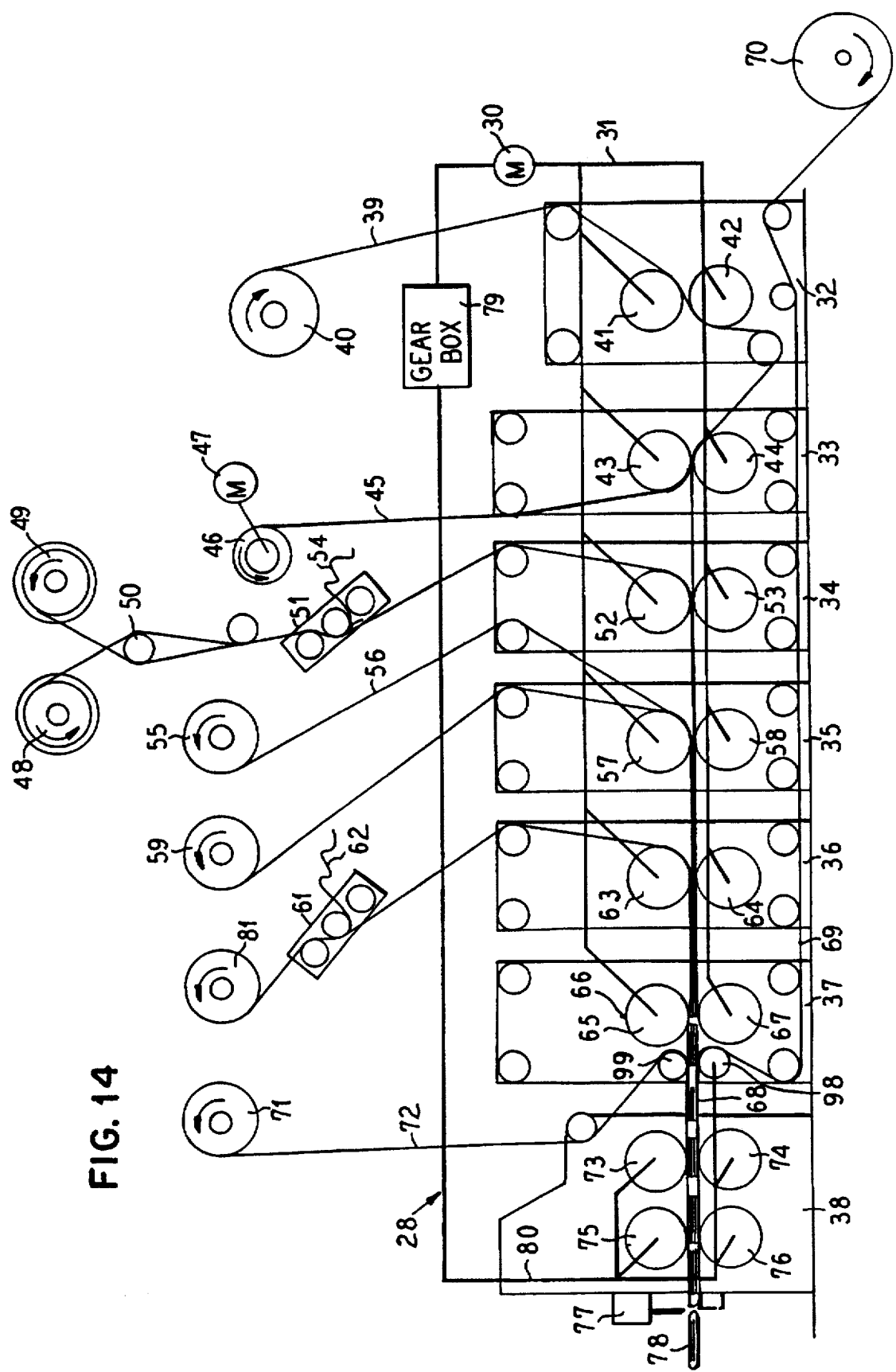

5,722,943

NON-STRETCHING WOUND DRESSING

This application is a continuation of application Ser. No. 07/417,289, filed Oct. 5, 1989 now abandoned which is a continuation of Ser. No. 797,777, filed on Nov. 12, 1985, now U.S. Pat. No. 4,884,563 issued on Dec. 5, 1989 which was a continuation-in-part of Ser. No. 707,233, filed on Mar. 1, 1985, abandoned.

BACKGROUND OF THE INVENTION

1. Field of the Invention

The present invention relates to wound dressings and methods for making same, and in particular to a wound dressing which can be applied to a patient without stretching thereof, and a method for the continuous production of a large number of such wound dressings.

2. Description of the Prior Art

Wound dressings consisting of thin flexible material, such as polyurethane, having adhesive on one side, which are applied to an open wound of a patient after medical treatment of the wound are known in the art. The flexible nature of the polyurethane permits the dressing to conform to virtually any contour of the patient at the location where the dressing is applied. The flexibility and thinness of the wound dressing, however, present the problem of applying the dressing to the patient without stretching the dressing. Stretching of the dressing prior to or during application thereof to a patient will momentarily expand the stretchable urethane, and even though the dressing may appear smooth when applied to the patient, the urethane will very quickly thereafter contract after the stretching forces are relieved, thereby causing discomfort to the patient and irritation to the area surrounding the wound. On weak or damaged skin, as in the elderly, the stretching forces can cause serious skin damage, such as an abcess. One proposed solution to the stretching problem was to use heavier polyurethane materials. These heavier materials are not desirable as a wound dressing due to decreased flexibility and less gas permeability.

Another proposed solution to this problem is to provide a flexible but non-stretching backing for the urethane wound dressing which remains in contact with the wound dressing by adhesive while the dressing is being applied to the patient, and is separated from the wound dressing only after the dressing has been placed on the patient, thereby eliminating stretching during application of the dressing. Such a wound dressing is described, for example, in European patent EP 0 066 899 A2. The wound dressing disclosed therein is a film sheet of polyurethane having adhesive on one side thereof which is applied to a patient. A non-stretchable film sheet carrier is pressed against the opposite side of the film sheet. The carrier may be bound to the film sheet either by the adhesion resulting from the polyurethane film sheet casting process, on a non-stretchable film sheet carrier or by a heat-dependent process to the non-stretchable carrier. A combination polyurethane film and MYLAR® polyester film (E. I. du Pont de Nemours, Wilmington, Del.) are commercially available. To this combination is added a free film of adhesive with the top adhesive backing left on the polyurethane film MYLAR® polyester film. Adhesive backing is peeled away prior to application to a patient. After the adhesive side of the film sheet is brought into contact with a patient, the Mylar® is peeled from the other side of the film sheet leaving polyurethane on the wound.

Another problem encountered when applying the polyurethane film to the wound is maintaining the sterility of the dressing during the application process. Previous products such as the polyurethane film wound dressings Ensure-It® (Deseret Medical, Inc.) and POLYSKIN® transparent dressing (Kendall Company, Boston, Mass.) required contact between fingers and the adhesive surface of the polyurethane film during application, thereby potentially contaminating the adhesive surface adjacent to the wound beneath the polyurethane.

Still another problem is the presence of a tab or tabs remaining on the polyurethane film after application to the wound surface. The presence of a tab often results in a gradual loosening of the polyurethane film to skin adhesive bond resulting in a curling-up of the polyurethane film edge adjacent to the tab.

One solution to this tab problem required a perforation adjacent to the tabs, thereby allowing removal of the tabs after application of the polyurethane film to the skin surface. However, the act of tearing of the tab perforations disturbs the adhesive bond, distorts or stretches the polyurethane film and microbially contaminates the adhesive, thereby resulting in a less secure, less sterile and less comfortable wound dressing.

There has been a long felt need for a polyurethane film product that provides ease of application, maintains sterility and does not require distortion of the film sheet by tearing operations. The tab systems of the present invention meet this need.

Alvarez et al., *Infections in Surgery*, p. 173, Mar. 1, 1984, presented evidence that a completely occlusive dressing such as hydrocolloid, best promoted the healing rate of wounds up to 96 hours. After longer periods of time, 96 hours or longer, a gas permeable polyurethane film resulted in superior healing rates as measured by collagen synthesis. These results suggest that for some applications the ideal wound dressing would function as a completely occlusive dressing for a first period of time, then function as a semi-occlusive dressing for a second period of time.

The layered construction of wound coverings containing gas permeable polymers has long experienced a problem in manufacturing. The casting of a polymer film sheet, such as polyurethane, on a casting sheet resulted in a weak electrostatic bond (corona coating) between the liner and polymer film sheet. This weak bond was weakly effective at holding the film sheet to the liner. If this liner was used as a cover sheet it was not-replaceable once removed. Wound coverings were limited to the types of liners that could be used as casting sheets for the polymer; such use requires resistance to casting heat. The most common liner being MYLAR® polyester film, a relatively stiff material not possessing the flexible properties desired in a material suitable for the application as a flexible wound cover contouring agent. A need existed for a production method allowing the insertion of adhesive and the substitution of a more flexible cover sheet.

SUMMARY OF THE INVENTION

It is an object of the present invention to provide a non-stretchable wound dressing which can be manufactured by overlying a series of continuous strips.

It is a further object of the present invention to provide such a wound dressing wherein the release characteristics between the wound dressing and the non-stretchable cover sheet can be controlled independently of the release characteristics between the wound dressing and the carrier sheet.

Another object of the invention is to provide a tab system that allows support of the non-stretchable wound dressing following removal of the carrier sheet. Still another object of the invention is to provide a tab system that allows manipulation of the wound dressing without contaminating contact between the sterile polyurethane film adhesive and the wound dressing applier's manipulating fingers. Yet another object of the invention is the presence of a tab system that prevents contact between the adhesive on the polyurethane film and the adhesive on the non-stretchable cover sheet, such contact being a source of defective applications. One object of the invention is the presence of a tab system that permits application of the wound dressing with one hand, such as self-application to the arm or hand. Another object of the invention is the optional presence of skin binding adhesive on the tabs of the non-stretchable cover sheet which permits the use of the cover sheet as a first 100% occluding wound cover, and following removal of this cover sheet, secondarily permits the semi-occluding polyurethane film to continue to cover the wound.

Yet another object of the invention is the coding of the tabs to indicate the sequential order of utilization of the tabs; Still another object of the invention is a wound dressing incorporating a hierarchy of adhesive strengths wherein the adhesive strength (1) of the bond between carrier sheet and polyurethane film is less than the adhesion strength (2) of the bond between the polyurethane film and the non-stretchable cover sheet, and this adhesion strength (2) is less than adhesive strength (3) of the bond formed between the polyurethane film adhesive and a biological surface or skin.

Yet another object of the invention is to provide a wound dressing wherein the film sheet contains an adhesive free area of less than 90% of the film sheet area, more preferably an adhesive free area of less than 50% of the film sheet area, and most preferably an adhesive free area of less than 30% of the film sheet area. Still another object of the invention is to provide a wound dressing wherein the film sheet contains an absorbent material covering less than 90% of the film sheet area, preferably less than 50% of the film sheet area and most preferably less than 30% of the film sheet area. The absorbent material may contain nothing; it may contain a medication such as an antibiotic, an anti-inflammatory compound, a pharmaceutical compound suitable for transdermal application, or a growth promoting hormone; and it may be opaque to block visualization of the wound and contain absorbent material as insulation to retain warmth in the wound region.

The above objects are inventively achieved in a non-stretchable wound dressing consisting of a thin film of material such as polyurethane having adhesive on one side thereof, and covered on the opposite side with a non-stretchable cover sheet, such as Mylar®, having two spaced tabs on opposite sides thereof, the adhesive side of the wound dressing is in contact with a release surface of a carrier, which may otherwise be comprised of heavy paper. Pulling the first gripping tab 1 lifts the combination wound dressing-cover sheet from the release surface of the carrier, and the second tab 2 provides another gripping area to place this combination over a wound without stretching the polyurethane sheet and without the necessity of the fingers of the person applying the dressing ever coming into contact with any part of the dressing which will be in contact with the patient, thereby avoiding transfer of dirt and infective microbes. After the combination wound dressing-cover sheet has been placed over the wound, the second tab 2 is pulled and, because the adhesive strength between the patient and the wound dressing is selected to have greater adhesive properties than the adhesive between the cover sheet and the wound dressing, the cover sheet is peeled away from the wound dressing, leaving it in place on the patient without stretching or wrinkling thereof. In one variation, a third tab 3 may be attached to a minor cover sheet located below the second tab 2, tab 2 being attached to the major cover sheet and tab 1.

Various different embodiments utilize a variety of agents and structures to promote easy release of the cover sheet from the wound dressing and/or of the wound dressing from the carrier sheet, among them gauze, and ink containing silicone or paraffin.

An object of the invention is a method of manufacturing wound coverings incorporating:

(a) a tab system for application, wherein roll stations continuously supply the materials for layered assembly of the tab system, and (b) formation of a packaging envelope as a final layered assembly step wherein the packaging roll stations increase the feed rate of top and bottom packing material wider than the wound coverings such that sufficient excess packing material between wound coverings permit the formation of a package seal capable of maintaining a sterile barrier around the enclosed wound covering.

This method for manufacturing a large number of such wound dressings has a plurality of stands or stations each having a pair of rolls forming a nip, and the upper roll of each station receiving at least one component of the wound dressing package in continuous feed from a supply roll. The various components in this strip form are applied over each other in connected layers. A last station cuts the continuous web of layers so as to produce the individual wound dressings, and the now-cut wound dressings are transferred onto a moving paper web which will form one side of a packaging envelope. The opposite side of the envelope is provided from above, sandwiching the wound dressings therebetween. The speed of the rolls at the station following the web cutting station is slightly higher than the speed of the preceding rolls, thereby providing increased spacing between the cut wound dressings. The top and bottom of the envelope webs are heat sealed or pressure sealed, and the spaces between the separated wound dressings are cut to form individual packaged dressings.

Another object of the invention is a manufacturing process wherein beneath the first tab, a narrow bond is formed between the film sheet adhesive and the cover sheet adhesive thereby insuring the successful removal of the cover sheet—film sheet combination from the carrier sheet upon pulling the first tab. A roller apparatus is utilized to exert pressure on the cover sheet just above the film sheet edge beneath the first tab, thereby insuring that sufficient adhesive bleeds out along the edge of the film sheet and forms a strong bond to the cover sheet adhesive.

Still another objective of the invention is a manufacturing process wherein beneath the second tab, a sheet of material is placed along the edge of the film sheet to insure that no bond is formed by the leaking of film sheet adhesive to contact the cover sheet adhesive. This prevention of a bond forming beneath the second tab, between the two adhesive layers, is critical to insure the reliable removal of the cover sheet from an undistorted film sheet after application to the patient surface. One method of preventing the bond between the adhesive layers beneath the second tab is the presence of a minor cover sheet over the film sheet edge. Attached beneath the inner edge of the minor cover sheet is third tab suitable for removing the minor cover sheet by pulling the third tab in a direction opposite the pulling direction of the second tab. The third tab—minor cover sheet system insures the easy removal of the major cover sheet by physically blocking the formation of a bond between the film sheet adhesive and major cover sheet adhesive. The minor cover sheet is held in place by a narrow band of cover sheet adhesive that binds along the top edge of the film sheet, but that does not extend adhesively to the extended minor carrier sheet.

Yet another object of the invention is a manufacturing process wherein the polyurethane film sheet is applied to a carrier such that the edges of the carrier sheet extend beyond the edges of the film sheet a distance suitable for gripping the extended carrier sheet as a tab but not touching film sheet surface.

DESCRIPTION OF THE DRAWINGS

FIG. 7 is a side view of one end of a further embodiment of a wound dressing constructed in accordance with the principles of the present invention;

FIGS. 8, 9, 10, 11, 12 and 13 are perspective views of one end of a wound dressing constructed in accordance with the principles of the present invention showing different embodiments for promoting release of the cover sheet from the film sheet; and FIG. 14 is a schematic side elevational view of an apparatus for manufacturing and packaging wound dressings in accordance with the method of the present invention in continuous feed.

DESCRIPTION OF THE PREFERRED EMBODIMENTS

The present invention meets a long felt need for a wound dressing that can be easily and safely applied. This wound dressing can be applied to any type of wound or to an intraveneous site (I.V. site). The transparent construction of the cover sheet and film sheet allow visual observation of the wound site during application and while on the patient. The cover sheet provides temporary 100% occlusion of the wound and can be removed easily using the two or three tab application systems. The cover sheet and tabs provide support for the wound dressing until after application. The cover sheet can then be removed without distorting or stretching the film sheet affixed to the patient surface or skin. If necessary, this wound dressing can be applied with one hand. The tabs are optionally marked with indicia indicating the order of utilization, thereby permitting error free application on the first attempt even by the inexperienced. The wound dressing may contain an area free of skin binding adhesive to allow easier removal from the wound area. The wound dressing may contain an absorbent material adjacent to the wound surface to absorb moisture or to allow delivery of medication. The wound dressing may be a surgical wrap suitable for application to protect the patient surface during surgery.

Figure 1:
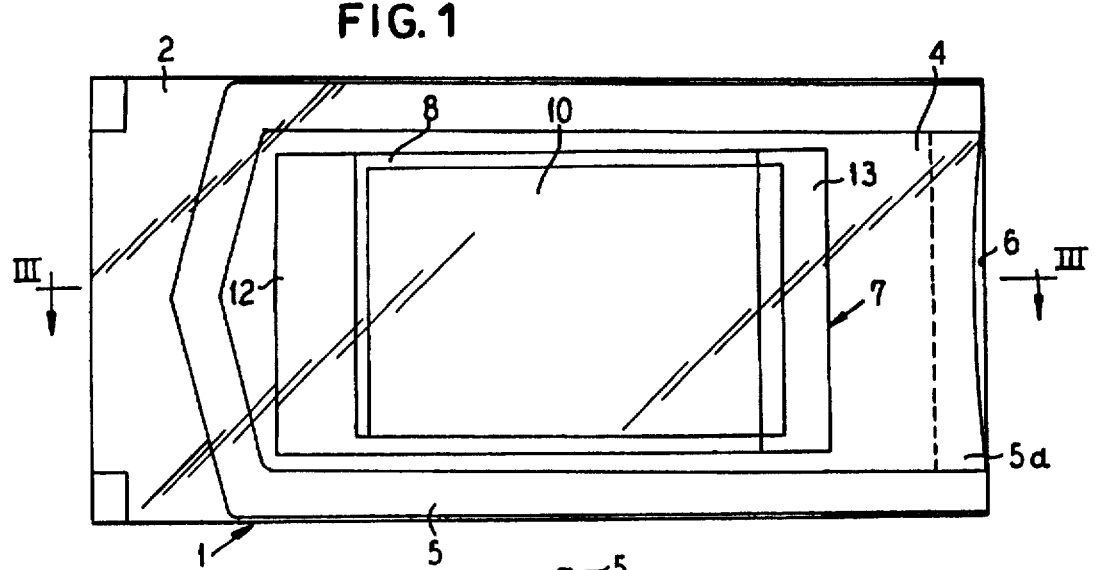
FIG. 1 is a plan view of a packaged wound dressing constructed in accordance with the principles of the present invention.
Figure 2:
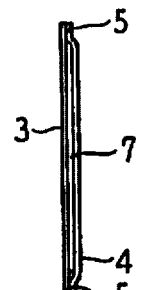
FIG. 2 is an end view of the packaged wound dressing shown in FIG. 1.

A packaged wound dressing constructed in accordance with the principles of the present invention is shown in FIG. 1 generally referenced at 1. The wound dressing 7 is contained in a package or envelope 2 consisting of a bottom 3 and a top 4, as best shown in FIG. 2. The bottom 3 and the top 4 are joined together at their margins on at least three sides by an adhesive zone 5 which surrounds but does not touch the wound dressing 7. The zone 5 may be produced by pressure, heat, adhesive, or any other suitable web joining means known to those skilled in the art. The bottom 3 and top 4 of the envelope 2 may be comprised of relatively heavy paper, or one of the pieces, such as the top 4, may be at least partially transparent so as to permit viewing of the wound dressing 7 therethrough. In the embodiment shown in FIG. 1, one end of the envelope 2 is unsealed, leaving an opening 6 for access to the wound dressing 7. It is also possible, however, to seal that end as indicated by the zone 5a. The two pieces 3 and 4 can be pulled apart with relatively little effort because the adhesive zone 5 (and 5a) is intentionally not particularly strong, and it is also possible to offset the zone 5a from the extreme edge of the envelope so as to provide a non-adhering flap or tab to provide a location to start the separation.

The strength of the adhesion bonds between the respective layers of the wound dressing are as follows. The carrier sheet to film sheet adhesive bond that is broken by pulling on the first tab has adhesion strengths from 0.01 to 4 grams/inch, preferably from 0.5 to 2 grams/inch, and most preferably 0.75 to 1.5 grams/inch. The inch measurements refer to the width of the wound covering perpendicular to the direction of tab removal.

The cover sheet to film sheet adhesive bond that is broken by pulling on the second tab is from 2 to 7 ounces/inch, preferably from 3 to 5 ounces/inch and most preferred from 3.5 to 4.0 ounces/inch.

The film sheet to skin adhesive bond that holds the film sheet to the patient has an adhesion strength when measured by a stainless steel 180° peel test of from 2 to 4.5 lbs. per inch.

Procedure for 180° Peel Adhesion Test

Measurement of the adhesive strength is accomplished by use of the PSTC #1 Test. Briefly, the test measures the tension when pulling a 1 inch×6 inch sample from a clean stainless steel plate while pulling at a 180° angle at a rate of 12 inches per minute. The test is accomplished on a Keil release tester or constant extension rate testing machine. The standard test conditions are 23°±2° C. and a relative humidity of 50%±2%.

A need has existed for a wound covering production method that included a gas permeable film sheet, such as polyurethane, on a carrier surface that positioned the film sheet at the center strip on a carrier with the carrier extending on either side. The casting sheet material used in the standard production method of polyurethane, is a material similar to Mylar®, the trademark for a polyester film, particularly polyethylene terephthalate. The casting sheet extending from end to end beneath the film sheet. To produce a region on either side of the casting sheet that is not covered by the film sheet, requires cutting of the film sheet and removal of the cut sides from the casting sheet.

If an adhesive is placed between this casting sheet, or a replacement carrier sheet, and the film sheet; then a silicone coating is required on the casting or carrier sheet to facilitate release of the casting or carrier sheet from the film sheet. With the silicone and adhesive in place, the cutting of the film sheet will damage the silicone coating on the casting or carrier sheet. This damage to the silicone results in binding of the adhesive to the casting or carrier sheet resulting in a defective wound covering.

The film sheet material may be urethane, copolymer or any flexible breathable polymer.

The production method of the present invention process allows the insertion of an adhesive layer between a casting sheet or a carrier sheet and the film sheet without the requirement of a cutting step to produce tabs at either side of the film sheet.

The procedures described in examples 1 and 2 describe the production of a two and three tab system for applying a wound covering. The method described allows the highly efficient production of such wound dressings that contain adhesive between the carrier and film sheet. These methods allow use of film sheet and adhesive free areas of the carrier for grasping to facilitate release of the cover sheet.

The use of the production methods of this invention allows more than a 10-fold production increase over previous methods, such as those of heat sealing the cover sheet to the film sheet.

EXAMPLE 1

Two Tab System

Figure 3:
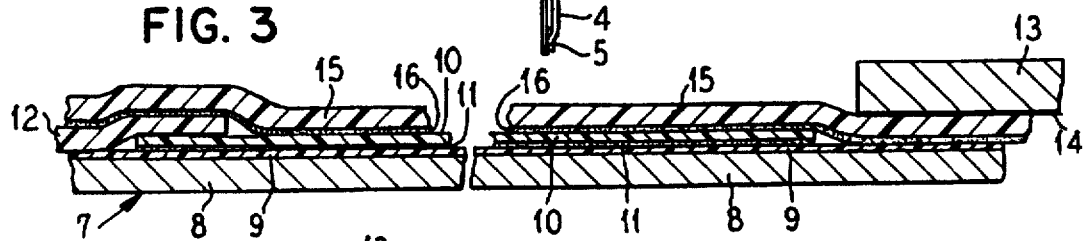
FIG. 3 is a side view, partly in section taken along line III—III, of the wound dressing in FIG. 1 with the package removed.

A first embodiment of the wound dressing with the envelope package removed is shown in FIG. 3, partly in section. The wound dressing 7 consists of a carrier sheet 8 which may be of plastic or relatively heavy paper. If the carrier sheet 8 is comprised of paper, one side of the carrier sheet 8 may be provided with a slick, smooth release surface 9. A film sheet 10, which will be used to cover the wound, is placed over the release surface 9 of the carrier sheet 8, the film sheet 10 having adhesive 11 on one side thereof adjacent the release surface 9. The side of the film sheet 10 not having adhesive thereon is in contact with an adhesive layer 16 carried on one side of a non-stretching but flexible cover sheet 15, which may be comprised, for example, of MYLAR® polyester film. A first gripping tab or strip 12 is bonded at one end of the cover sheet 15 by any suitable adhesive. A second gripping tab or strip 13 is carried at an opposite end and on an opposite side of the cover sheet 15, connected thereto by any suitable bond schematically represented at 14.

Figure 5:
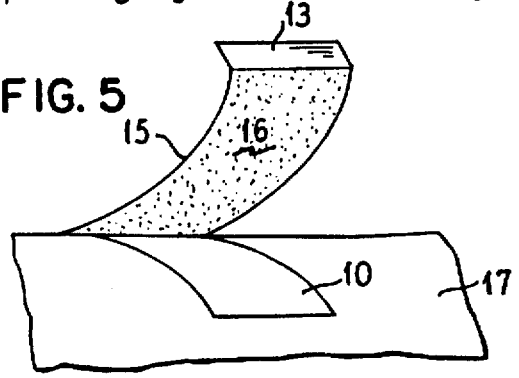
FIG. 5 shows a second step in applying the wound dressing of FIG. 1 to a patient.
Figure 4:
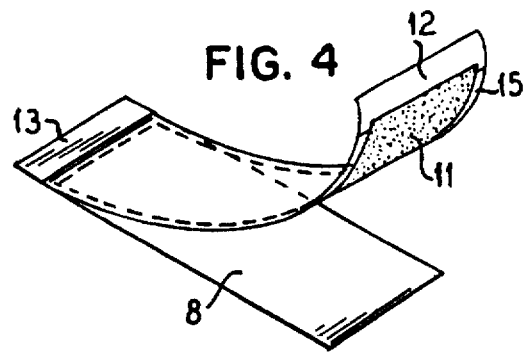
FIG. 4 shows a first step in applying the wound dressing of FIG. 1 to a patient.

Application of the wound dressing to a portion 17 of a patient is shown in FIGS. 4 and 5. The tab 12 is gripped and pulled. By the combination of the release surface 9 and the relative strengths of the adhesive layers 11 and 16, pulling on the gripping tab 12 causes release of the adhesive layer 11 from the release surface 9, with the cover sheet 15 still adhering to the opposite side thereof. This combination is then placed over the wound of a patient, with the person applying the dressing gripping the opposite end of the cover sheet 15 at the gripping tab 13. The fingers of the person applying the wound dressing therefore need never come into contact with the adhesive layer 11 which will be placed against the patient's skin. Once in place, the adhesion of the layer 11 to the patient's skin is greater than the adhesion via the layer 16 between the cover sheet 15 and the film sheet 10, thus as shown in FIG. 5, and tab 13 can be pulled thereby removing the cover sheet 15 and leaving the film sheet 10 adhering to the patient. This release can be accomplished solely by selecting the relative strengths of the adhesive layers 11 and 16, or can be assisted and promoted by various agents and structures shown in the embodiments discussed below.

Figure 6:
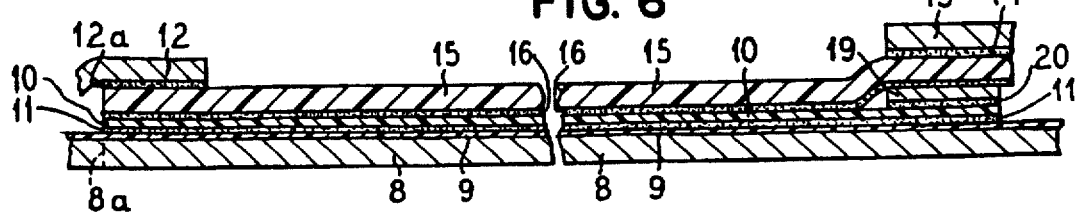
FIG. 6 is a side view of a further embodiment of a wound dressing constructed in accordance with the principles of the present invention.

Another embodiment of a wound dressing constructed in accordance with the principles of the present invention with the package removed is shown in side elevational view in FIG. 6. Components thereof which are identical to the embodiment shown in FIG. 3 are identified with the same reference numerals. In this embodiment, the gripping tab 12 is on the upper side of the cover sheet 15, being affixed thereto by any suitable bonding, schematically represented at 12a. The carrier sheet 8 may be scored along a line 8a to promote pulling of the tab 12, which extends slightly beyond the film sheet 10. Pulling the tab 12 again releases the combination of the cover sheet 15 with the film sheet 10 adhering thereto from the carrier sheet 8. This combination is again placed over the wound, and the tab 13, which may extend beyond the opposite end of the film sheet 10 is pulled to release the cover sheet 15 from the film sheet 10. Release may be promoted by a gauze or paper strip 19 affixed to the non-adhesive side of the film sheet 10 by a bonding of any suitable type schematically represented at 20. The strip 19 remains in place when the film sheet 10 is on the patient, however, the strip 19 is sufficiently flexible so as not to interfere with the ability of the film sheet 10 to conform to the contour of the patient. One source of material for strip 19 is the MICROPURE® surgical adhesive tape (3M Corporation, St. Paul, Minn.). The presence of strip 19 ensures the even application of the wound dressing to the patient surface by promoting evenly distributed tension between the cover sheet 15 and the film sheet 10 as it is released by pulling on tab 13. This even release ensures that the film sheet 10 will not be distorted by excessive distorting stress on any one region of the film sheet.

Yet another embodiment of one end of the wound dressing is shown in FIG. 7, wherein the tab 12 is beneath the film sheet 10, interposed between the adhesive layer 11 and the release surface 9 to promote the initial separation of the film sheet 10 from the carrier sheet 8.

Various embodiments showing different means for promoting release of the cover sheet 15 from the film sheet 10 once the film sheet 10 is in place over a portion 17 of a patient are shown in FIGS. 8 through 13. In FIG. 8, this means consists of a plurality of inked lines 21 printed over the adhesive layer 16. This provides sufficient interruption of the adhering properties of the adhesive layer 16 to facilitate easy removal. In the embodiment of FIG. 9, the release promoting means consists of a laterally inked zone 22 printed over the adhesive 16.

The inked zone is made by applying an ink containing an adhesive deadening agent. Among the adhesive deadening agents are silicone and paraffin. Ink is applied to the adhesive area to be deadened until 50% to 95% of the adhesive bond is lost, or more preferably 70% to 92% of the adhesive bond is lost; and most preferably 80% to 90% of the adhesive bond is lost.

In FIG. 10 the release promoting means consists of a plastic or fiber mesh 23.

In the embodiment of FIG. 11, the release promoting means consists of a smooth slick strip 24 which can either be left in place if made suitably narrow, or can be peeled away if desired.

In the embodiment of FIG. 12, the release promoting means is a paper strip 25 having a series of perforations 26 therein.

EXAMPLE 2

Three Table System

The general layered structure of Example 1 is repeated in the three tab system, except the release material 19 in FIG. 6 is functionally replaced by a third tab attached to a flexible sheet 27 in FIG. 13.

Figure 15:
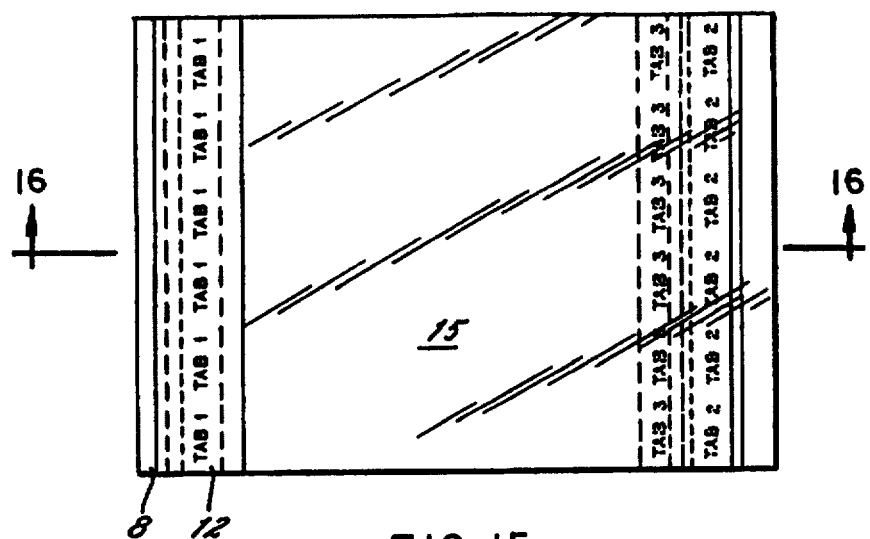
FIG. 15 is a top view of the three tab system wound covering.
Figure 16:
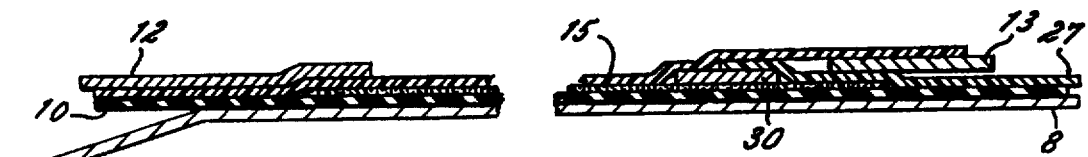
FIG. 16 is a sideview taken in section along the lines indicated in FIG. 15 marked 2.
Figure 17:
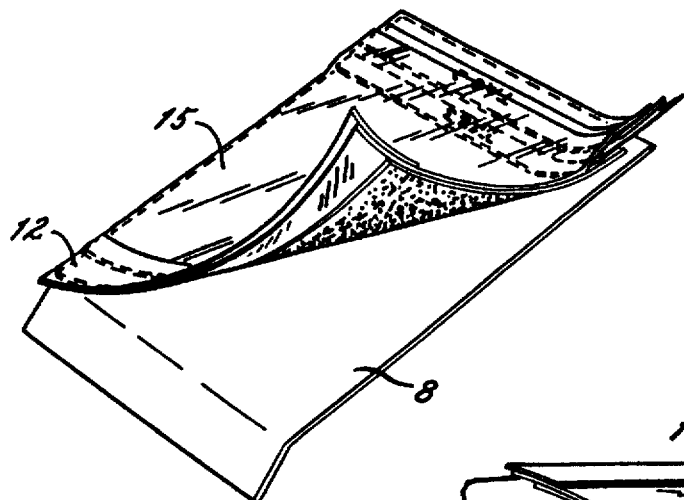
FIG. 17 is a view of the three tab system showing the removal of the non-stretching carrier sheet and film sheet by pulling on the first tab.
Figure 18:
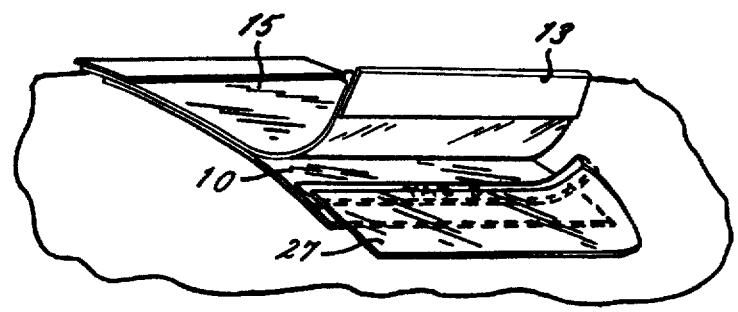
FIG. 18 is a view of the film sheet adhesively bound to the skin with the second tab being removed to leave the film sheet on the skin surface, the third tab has been lifted in the right corner to demonstrate how removal of the third tab and minor cover sheet is accomplished.

In the embodiment of FIG. 13, the release promoting means is not affixed to the adhesive 16, but is rather interposed between the adhesive layer 16 and the non-adhesive side of the film sheet 10. In this embodiment, a flexible sheet 27 has a release surface 28 which is interrupted in the zone indicated by the arrow 29. Normally the portion of the sheet 27 overlying the film sheet 10 is covered by the tab 13, however, when the tab 13 is pulled away, that portion of the sheet 27 is exposed and the non-adhering portion at the surface 28 provides a third tab to pull the remainder of the sheet 27 away, leaving the film sheet 10 in place on the patient. The third tab may be only the flexible sheet 27 as illustrated in FIG. 13 or it may have a tape tab affixed above or below the flexible sheet 27 in the region 28. In FIG. 15 a top view is shown illustrating the relative positions of the first tab (tab 1), the second tab (tab 2) and the third tab (tab 3). A cross section of FIG. 15 is shown in FIG. 16 which illustrates the positions of the third tab 30 beneath both the sheet 27 and the major cover sheet 15. The first tab 12 in FIG. 16 is lifted to remove the cover sheet 15 from the carrier sheet 8. This lifting of the first tab is illustrated in FIG. 17. After the wound dressing is applied to the wound, the second tab 13 (FIG. 16) is lifted to remove the major cover sheet 15. FIG. 18 illustrates the lifting of the second tab and major cover sheet to expose the third tab and minor cover sheet. In FIG. 16 the third tab 30 is exposed when the second tab 13 is lifted to remove the major cover sheet. The minor cover 27 is removed by pulling the third tab 30 in a direction opposite to the direction the second tab was pulled. This is illustrated by FIG. 18 where the right corner of tab 3 is being lifted to remove the minor cover sheet and leave a completely applied film sheet on the wound area without stressed areas or microbial contamination of the wound area.

All three tabs may bear an indicia indicating the order of use. The third tab may bear an indicia indicating it is the third tab in the three tab system. Similarly the first tab 12 may contain an indicia incidating it is the first tab in the three tab system and tab 13 may contain an indicia indicating it is the second tab in the three tab system. Indicia useful for marking on the three tab system include 1, 2, 3; I, II, III; A, B, C; Tab 1, Tab 2, Tab 3; First, Second, Third; Pull First, Pull Second, Pull Third; and other analogous instructions that allow the error free application of the wound dressing. This three tab system allows the application of the wound dressing using only one hand, particularly valuable for self-application to the hand or arm. Two hands are used to remove the carrier sheet 8, by holding the first tab 12 and the second tab 13 then the free hand applies the wound dressing and removes the flexible cover sheet 15 by pulling on the second tab. The third tab in region 28 of FIG. 13 is then pulled to leave the tab free wound dressing on the patient.

A suitable material for the film sheet 10 is urethane number 5020 available from Avery International, Fasson Industrial Division, of Plainesville, Ohio.

EXAMPLE 3

Wound Covering with Adhesive Free Area

The wound coverings of Examples 1 and 2 can be produced with an area free of the patient binding adhesive layer 11 (FIGS. 3, 6, 13). An adhesive free area is useful in wound coverings in that the wounded tissue may better heal if not in direct contact with adhesive. In addition, the removal of the film sheet 10 (FIGS. 3, 6, 13) from the wound surface can cause additional trauma to the healing wound surface. The adhesive free area may be less than 95% of the surface area of the film sheet 10, preferably less than 50% of the area of film sheet 10, and most preferably it is less than 30% of the area of film sheet 10. The adhesive free area may be prepared by any of several methods known in the adhesive industry. One method is the modification of the adhesive bearing web 39. (FIG. 14) before it is applied to the exposed side of the film sheet. A silicone coated cover sheet is mated with the adhesive bearing web 39 to reversibly enclose the adhesive layer between two silicon coated materials. A die of the desired shape (square, circle, diamond, ellipse, etc.) and of the desired area is used to punch out a hole in the adhesive plus enclosing material. The silicone coated cover sheet is then removed and the adhesive layer (web 39) is applied to the film sheeting as described in Example 5.

EXAMPLE 4

Absorbent Pad Containing Wound Covering

The wound coverings of Examples 1, 2 and 3 may be modified to contain an area of hydrophilic absorbent material. The area of absorbent material may cover less than 95% of the surface area of the film sheet 10 (FIGS. 3, 6, 13), more preferable the absorbent material may cover less than 50% of the surface area of film sheet 10, most preferably the absorbent material may cover less than 30% of the surface area of film sheet 10. The absorbent material may be of any desirable shape including a square, rectangle, circle, diamond or ellipse. The absorbent material may contain nothing in which case it is suitable for absorbing moisture from the wound area.

The absorbing material may contain medication. The medication may be an antibiotic, a healing promoting agent, an anti-inflammatory agent, a transdermal diffusable pharmaceutical, a coagulant or an anti-coagulant. Among the anticipated antibiotics are typical bacteriostatic and bactericidal agents, anti-fungal and anti-viral agents. Among the anti-bacterial agents and anti-fungal agents are the penicillins, streptomycins, sulfuramides, cephalosporins, kanamycins, gentamicin, tobramycin, neomycin, paromomycin, chloramphenicol, tetracyclines, lincomycin, novobiocin, nalidixic acid, rifamycins, polymyxin B, griseofulvin, pimaricin, conystatin, amphotericin B; and for viruses rifamycin, nucleic acid analogs, arabinosyl thymine, 5-iodo-5'amino-2'-5'dideoxycridine, arabinosyl adenine, arabinosyl cytosine, acycloguanosine, ribavirin, phosphono acetic acid, and idoxuridine. Among healing promoting agents are growth promoting hormones, among them epidermal growth factor and urogastrone. Among the anti-inflammatory agents are the corticosteroids. Among the transdermal diffusable pharmaceuticals are nitroglycerin, and other cardiac and blood pressure effecting agents. Among the coagulants are the blood clotting factors and activators of the intrinsic or extrinsic clotting pathways. Among the anti-coagulants are heparin, citric acid, protamine sulfate, and other inhibitors of blood clotting. Also useful as anti-blood clotting agents are thrombolytic enzymes such as streptokinase and urokinase.

The presence of an absorbent material or a hydrophilic absorbent material patch not only serves as an absorbent, it also serves as an insulating material that holds the body's warmth at the wound site. This increase warmth due to the patch facilitates a more rapid healing of the wound. If an absorbent material patch is present under a gas permeable wound dressing, and the moisture or medication on the patch is subject to excessive drying, a gas impermeable piece of material, such as polyethylene, can be placed over the absorbent patch area to decrease moisture loss.

An advantage of the use of adhesive to bind the cover sheet to film sheet is the ability to rebind the cover sheet to the film sheet. This allows inspection of the wound when vision is impeded by the cover sheet. The ability to remove the cover sheet for inspection is particularly useful in intraveneous punctures where the needle site must be regularly inspected. Visual inspection of the wound and replacement of the cover sheet is useful in applications with children, colostomy devices, burns and any situation when inspection is required, but a return of the gas impermeable cover sheet is desirable.

The absorbent material may be gauze, sponge or other inert absorbent material. The absorbent material may be clear or opaque to conceal the wound area. Among the hydrophilic absorbent materials are poly (D-Glucosamine) from Bentech Laboratories and ARASORB 720® superabsorbent polymer (Arakawa Chemical Inc., Chicago, Ill.).

EXAMPLE 5

Two Stage Wound Covering

In another embodiment of the invention, the wound covering of Examples 1, 2, 3 and 4 contains skin binding adhesive beneath the first tab (12, FIGS. 3, 6 and 13) and beneath the second tab (13, FIGS. 3, 6 and 13). This skin binding adhesive is of a strength similar to that on the film sheet (10) and permits the cover sheet to remain on the patient for a period up to 96 hours to allow gas impermeable, 100% occluded wound healing. The cover sheet can then be removed to allow the gas permeable film sheet (10) to remain on the wound for an additional period of time. This two stage wound covering allows flexibility in regulating the period of time the wound area will be covered by gas permeable and gas impermeable wound coverings without the need to change the wound covering in contact with the patient.

EXAMPLE 6

Tab System Surgical Drape

The wound coverings of Examples 1, 2 and 3 may be in the form of a surgical drape or wrap suitable for application to the surface of a patient before surgical procedures. The surgical wrap may contain a film sheet 10 (FIGS. 3, 6, and 13) that is either gas permeable or gas impermeable. It may be constructed of polyurethane or other gas permeable materials. It may be constructed of polyethylene or other gas impermeable materials. The tab systems permit the easy application to the patient surface with the tabs providing additional support to the flexible cover, allowing easy manipulation and placement at the appropriate location. The dimensions of the surgical wrap are variable and range from 1 inch×2 inches to 24 inches×36 inches.

EXAMPLE 7

Method for Wound Covering Production

An apparatus for undertaking the method disclosed herein for continuous production of wound dressings of this type solely from web material is shown in FIG. 14. The apparatus is generally referenced at 28 and has first motor 30 with a drive train schematically represented at 31 for rotating rollers comprising successive nips in stations or stands 32, 33, 34, 35, 36 and 37. Although in FIG. 14 both rollers in each nip are shown as driven by the motor 30, it is possible to operate the apparatus 28 with only one roller, such as the upper roller, in each nip being driven. A web of film sheet adhering to a liner is supplied from supply reel 40, the combination film sheet and liner web being indicated at 39. This web 39 passes between rollers 41 and 42 wherein an adhesive is applied to the exposed side of the film sheet. The web continues to the next station 33, passing through rollers 43 and 44 with the sheet transferring to roller 44 and the liner transferring to the roll 43. The now-separated liner 45 is received on a take up roll 46, which may be separably driven by a motor 47. The film sheet continues to station 34 wherein it is joined with the carrier sheet which has two tabs on each side thereof supplied from reels 48 and 49, passing around roll 50. The liner on which the tabs were originally carried is separated by a doctor assembly 51 and the liner 54 is disposed of. In the next station the inside paper tab supplied in web form 56 from a reel 55, passing through rollers 57 and 58 in station 35. The cover sheet is also supplied in web form to station 35 from a reel 59. The outside paper tab is then supplied from a reel 81 in station 36 between rolls 63 and 64. The liner 62 originally carrying the tabs is removed therefrom by a doctor assembly 61.

At this point, a continuous layered web has been constructed in the successive stations. The web in station 37 passes through a cutting nip formed by rolls 65 and 67, one of the rolls having a blade 66 thereon. Because the blade 66 simply cuts the continuous web, and results in very little space between the cut pieces, another drive train schematically represented at 80 is utilized to drive the rolls in station 38 and rolls 98 and 99 at a speed greater than the speed of the outer rolls in stations 32–37. Again, it may only be necessary to drive one roll in each nip, such as the upper rolls. A motor may be used to drive the rolls 98 and 99 and the rolls in station 38, at a faster speed than the motor 30 drives the other rolls; however usually the drive train 80 is connected by a gear box 79 to the motor 30. One portion of the package envelope is supplied from a supply reel 70 to the roll 98 and the cut wound dressings 68 pass an open draw following the nip formed in station 37 and are laid upon the faster moving envelope web 69, thereby increasing the spacing between the pieces 68. A top of the envelope package in web form 72 supplied from a reel 71 to the roll 99, and suitable bonding of the top and bottom portions with the wound dressings 68 therebetween is accomplished by rolls 73 and 74, and rolls 75 and 76 in station 38. A cutter 77, synchronized to the spacings between the wound dressings 68, severs the sealed envelopes, resulting in individual packages 78, of the type shown in FIG. 1.

The following examples of the types of wound coverage are illustrations of the tab systems and wound coverings of this invention. They do not limit the scope of wound dressings anticipated.

The size ranges of wound dressings can vary from 0.20× 1.0 inch to 18×18 inches. Preferred sizes of wound dressing are 1"×3", 2"×3", 3"×4", 4"×5", 6"×8", 10"×12", 12"×18".

Although modifications and changes may be suggested by those skilled in the art it is the intention of the inventor to embody within the patent warranted hereon all changes and modifications as reasonably and properly come within the scope of his contribution to the art.

I claim as my invention:

1. A non-stretching wound dressing comprising:
    a one-piece carrier sheet;
    a film sheet having a first adhesive layer on one side thereof adjacent said carrier sheet;
    a cover sheet having a second adhesive layer adjacent said film sheet, said second adhesive layer adhering said cover sheet to said film sheet and covering essentially all of one side of said cover sheet;
    a first gripping tab on one end of said cover sheet for separating and removing said carrier sheet from said film sheet and from said wound dressing with said cover sheet remaining affixed to said film sheet, said adhesion between said cover sheet and said film sheet being selected such that pulling said first tab releases said film sheet from said carrier sheet with said cover sheet remaining affixed to said film sheet; and
    a second gripping tab on an opposite end of said cover sheet from said first gripping tab for releasing said cover sheet from said film sheet, said adhesion between said cover sheet and said film sheet being further selected such that, after removal of said carrier sheet from said wound dressing and application of the adhesive side of said film sheet to a patient, pulling on said second tab releases said cover sheet from said film sheet with said film sheet remaining in place on said patient.

2. A wound dressing according to claim 1 wherein said film sheet contains an absorbent material covering less than 95% of the film sheet.

3. A wound dressing according to claim 1 wherein said film sheet is polyurethane.

4. A wound dressing according to claim 1 wherein said carrier sheet includes a release layer on the surface thereof adjacent said adhesive layer on said film sheet.

5. A wound dressing according to claim 1 wherein the strengths of adhesion are selected such that a first adhesion between said carrier sheet and said film sheet is less than a second adhesion between said cover sheet and said film sheet and said second adhesion is less than a third adhesion between said film sheet and a biological surface of the patient to which the wound dressing is applied.

6. A wound dressing according to claim 1 wherein said film sheet is gas-permeable.

7. A wound dressing according to claim 1 including a means for promoting release of said cover sheet from said film sheet positioned beneath said second tab.

8. A non-stretching wound dressing comprising:
    a one-piece carrier sheet;
    a film sheet having an adhesive layer on one side thereof adjacent said carrier sheet;
    a cover sheet adhered to said film sheet;
    a first gripping tab on one end of said cover sheet for separating and removing said carrier sheet from said film sheet and from said wound dressing with said cover sheet remaining affixed to said film sheet, said adhesion between said cover sheet and said film sheet being selected such that pulling said first tab releases said film sheet from said carrier sheet with said cover sheet remaining affixed to said film sheet;
    a second gripping tab on an opposite end of said cover sheet from said first gripping tab for releasing said cover sheet from said film sheet, said adhesion between said cover sheet and said film sheet being further selected such that, after removal of said carrier sheet from said wound dressing and application of the adhesive side of said film sheet to a patient, pulling on said second tab releases said cover sheet from said film sheet with said film sheet remaining in place on said patient; and
    said first and second gripping tabs having indicia indicating the sequential order of use.

9. A wound dressing according to claim 8 wherein said film sheet contains an absorbent material covering less than 95% of the film sheet.

10. A wound dressing according to claim 8 wherein said film sheet is polyurethane.

11. A wound dressing according to claim 8 wherein said carrier sheet includes a release layer on the surface thereof adjacent said adhesive layer on said film sheet.

12. A wound dressing according to claim 8 wherein the strengths of adhesion are selected such that a first adhesion between said carrier sheet and said film sheet is less than a second adhesion between said cover sheet and said film sheet and a second adhesion is less than a third adhesion between said film sheet and a biological surface of the patient to which the wound dressing is applied.

13. A wound dressing according to claim 8 wherein said film sheet is gas-permeable.

14. A wound dressing according to claim 8 including a means for promoting release of said cover sheet from said film sheet positioned beneath said second tab.

15. A non-stretching wound dressing comprising:
    a carrier sheet;
    a film sheet having a first adhesive layer on one side thereof adjacent said carrier sheet;
    a cover sheet positioned on at least a central portion of said film sheet and having a second adhesive layer adjacent said film sheet, said second adhesive layer adhering said cover sheet to said film sheet;
    a first gripping tab separate from and directly attached to one end of said cover sheet for separating and removing said carrier sheet from said film sheet and from said wound dressing with said cover sheet remaining affixed to said film sheet, said adhesion between said cover sheet and said film sheet being selected such that pulling said first tab releases said film sheet from said carrier sheet with the cover sheet remaining affixed to said film sheet; and
    a second gripping tab on an opposite end of said cover sheet from said first gripping tab for releasing said cover sheet from said film sheet, said adhesion between said cover sheet and said film sheet being further selected such that after removal of said carrier sheet from said wound dressing and application of the adhesive side of said film sheet to a patient, pulling on said second tab releases said cover sheet from said film sheet with said film sheet remaining in place on said patient.

16. A non-stretching wound dressing according to claim 15 wherein said first and second gripping tabs have an indicia indicating the sequential order of use.

17. A surgical drape suitable for application to the surface of a patient comprising:

a one-piece carrier sheet;

a film sheet having a first adhesive layer on one side thereof adjacent said carrier sheet;

a cover sheet having a second adhesive layer adjacent said film sheet, said second adhesive layer adhering said cover sheet to said film sheet and covering essentially all of one side of said cover sheet;

a first gripping tab on one end of said cover sheet for separating and removing said carrier sheet from said film sheet and from said surgical drape with said cover sheet remaining affixed to said film sheet, said adhesion between said cover sheet and said film sheet being selected such that pulling said first tab releases said film sheet from said carrier sheet with the cover sheet remaining affixed to said film sheet; and a second gripping tab on an opposite end of said cover sheet from said first gripping tab for releasing said cover sheet from said film sheet, said adhesion between said cover sheet and said film sheet being further selected such that, after removal of said carrier from said surgical drape and application of the adhesive side of said film sheet to a patient, pulling on said second tab releases said cover sheet from said film sheet with said film sheet remaining in place on said patient.

18. A surgical drape according to claim 17 wherein said film sheet comprises a polyethylene sheet.

19. A surgical drape suitable for application to the surface of a patient comprising:

a one-piece carrier sheet;

a film sheet having a first adhesive layer on one side thereof adjacent said carrier sheet;

a cover sheet adhered to said film sheet;

a first gripping tab on one end of said cover sheet for separating and removing said carrier sheet from said film sheet and from said surgical drape with said cover sheet remaining affixed to said film sheet, said adhesion between said cover sheet and said film sheet being selected such that pulling said first tab releases said film sheet from said carrier sheet with the cover sheet remaining affixed to said film sheet; and a second gripping tab on an opposite end of said cover sheet from said first gripping tab for releasing said cover sheet from said film sheet, said adhesion between said cover sheet and said film sheet being further selected such that, after removal of said carrier from said surgical drape and application of the adhesive side of said film sheet to a patient, pulling on said second tab releases said cover sheet from said film sheet with said film sheet remaining in place on said patient; and said first and second gripping tabs having indicia indicating the sequential order of use.

20. A surgical drape according to claim 19 wherein said film sheet comprises a polyethylene sheet.

21. A wound dressing according to claim 1 wherein said carrier sheet and said first gripping tab on said cover sheet are so constructed and arranged that said cover sheet may be removed with one hand.

22. A non-stretching wound dressing according to claim 1 wherein said cover sheet is positioned on at least a central portion of said film sheet.

23. A non-stretching wound dressing according to claim 1 wherein said cover sheet is substantially coextensive with said film sheet.

24. A surgical drape suitable for application to the surface of a patient according to claim 17 wherein said cover sheet is positioned on at least a central portion of said film sheet.

25. A surgical drape suitable for application to the surface of a patient according to claim 17 wherein said cover sheet is substantially coextensive with said film sheet.

26. A non-stretching wound dressing comprising:

a carrier sheet;

a film sheet having a first adhesive layer on one side thereof adjacent said carrier sheet;

a cover sheet substantially coextensive with said film sheet and having a second adhesive layer adjacent said film sheet, said second adhesive layer adhering said cover sheet to said film sheet;

a first gripping tab separate from and directly attached to one end of said cover sheet for separating and removing said carrier sheet from said film sheet and from said wound dressing with said cover sheet remaining affixed to said film sheet, said adhesion between said cover sheet and said film sheet being selected such that pulling said first tab releases said film sheet from said carrier sheet with the cover sheet remaining affixed to said film sheet; and a second gripping tab on an opposite end of said cover sheet from said first gripping tab for releasing said cover sheet from said film sheet, said adhesion between said cover sheet and said film sheet being further selected such that after removal of said carrier sheet from said wound dressing and application of the adhesive side of said film sheet to a patient, pulling on said second tab releases said cover sheet from said film sheet with said film sheet remaining in place on said patient.

\* \* \* \* \*